United States Patent [19]

Nash

[11] Patent Number: 5,030,737

[45] Date of Patent: Jul. 9, 1991

[54] USE OF A SOLVENT FOR HYDROGENATION OF SULFOLENE TO SULFOLANE

[75] Inventor: Martin E. Nash, Borger, Tex.

[73] Assignee: Phillips Petroleum Company, Bartlesville, Okla.

[21] Appl. No.: 478,903

[22] Filed: Feb. 12, 1990

[51] Int. Cl.$^5$ ............................................ C07D 333/48
[52] U.S. Cl. ..................................................... 549/87
[58] Field of Search .......................................... 549/87

[56] References Cited

U.S. PATENT DOCUMENTS 2,578,565 12/1951 Mahan et al. .
3,152,144 10/1964 Middlebrook .
3,345,384 10/1967 Oelderik et al. .
3,514,469  5/1970 Phillips et al. .
3,770,772 11/1973 Kroll .
3,998,845 12/1976 Goldstein et al. .
4,188,327  2/1980 Kubicek .
4,275,218  6/1981 Huxley et al. .
4,286,099  8/1981 Nash et al. .

*Primary Examiner*—Alan Siegel
*Attorney, Agent, or Firm*—Charles W. Stewart

[57] ABSTRACT

A process for converting a sulfolene feed, containing contaminating amounts of sulfur dioxide, to a sulfolane product in which the sulfolene feed is dissolved in a solvent selected from the group consisting of alcohols and ketones having at least six carbon atoms per molecule, slight solubility in water and a boiling point significantly above 100° C., the thus formed sulfolene solution is distilled to reduce the sulfur dioxide content, the sulfolene solution and hydrogen are contacted with a hydrogenation catalyst to convert the sulfolene feed to a sulfolane product and the sulfolane product is recovered from the effluent of the contacting step.

17 Claims, 1 Drawing Sheet

USE OF A SOLVENT FOR HYDROGENATION OF SULFOLENE TO SULFOLANE

The present invention relates to the production of sulfolane. In accordance with another aspect of the present invention, it further relates to an improved process for the pretreatment of a sulfolene-containing feed and the conversion of said sulfolene feed to sulfolene. In a more specific aspect, the present invention relates to the pretreatment of a sulfolene-containing feed and the hydrogenation of sulfolene to sulfolane in the presence of an improved solvent.

Sulfolane compounds are useful for a variety of purposes such as in pesticidal compositions, intermediates in the production of other organic chemicals, the extraction of aromatic hydrocarbons from refinery streams, fractionation of wood tars, coal oil and other fatty acids, a polymerization solvent, a plasticizer, a component of hydraulic fluids, textile finishing and the like. Sulfolane compounds are generally prepared by the catalytic hydrogenation of the corresponding sulfolene compounds. These sulfolene compounds are in turn generally prepared by reaction of sulfur dioxide with a sulfolene precursor such as conjugated diene, thus producing a sulfolene compound which generally contains minor amounts of sulfur dioxide as well as a polymeric material generally described as "polysulfone". In the subsequent hydrogenation of the feed to sulfolane products, the sulfur dioxide and polysulfones present therein poison or coat the hydrogenation catalyst and significantly reduce the activity thereof.

Prior art workers have recognized problems associated with the hydrogenation of sulfolene compounds containing sulfur dioxide and polysulfones. Accordingly, several techniques have been suggested for reducing the amount of sulfur dioxide and polysulfones in sulfolene feed compounds prior to the hydrogenation thereof to sulfolanes. For example, it has been suggested that the sulfolene feed be treated with hydrogen peroxide, alkali metal peroxides, and tertiary amines. Another suggested approach is to subject sulfolene feed to reduced pressure to remove some of the sulfur dioxide and then treat with calcium oxide or hydroxide or magnesium oxide or hydroxide to convert the remaining sulfur dioxide to partially insoluble sulfite salts which can then be removed by filtration. However, such pretreatments are generally only partially effective, and they often add to the expense and time required for hydrogenation and recovery of product sulfolanes.

Since sulfolenes are normally solid materials, it is also necessary that the sulfolene compound be in a liquid state or solution in order to carry out the hydrogenation reaction. For example, the sulfolene must be maintained in a molten state above its melting point but below its thermal decomposition temperature, which is generally about 100° C. The common practice is to form a solution of the sulfolenes in a suitable solvent, such as water, benzene, dioxane, alcohols, such as methyl, ethyl, isopropyl, or tertiary butyl alcohol, the sulfolane compound itself and the like. The most common solvent is water. However, the utilization of a solvent can also cause problems during the hydrogenation reaction, such as increasing catalyst requirements, and increasing the time necessary for hydrogenation. Furthermore, the type of solvent used in carrying out the hydrogenation reaction can dramatically impact the efficiency of recovery of the sulfolane products.

SUMMARY OF THE INVENTION

It is therefore an object of the present invention to provide an improved process for purifying a sulfolene-containing material and to provide an improved process for hydrogenating a sulfolene-containing material.

Another object of the present invention is to provide an improved process for purifying a sulfolene-containing material which removes substantially all of the $SO_2$ impurities therefrom.

Another further object of the present invention is to provide an improved process for removing $SO_2$ from a sulfolene-containing material.

Yet another object of the present invention is to provide an improved method for the removal of polysulfones from sulfolene-containing materials.

Another further object of the present invention is to provide an improved process for removing contaminants from a sulfolene-containing material in the presence of a solvent and reducing the loss of solvent in such process.

Yet another object of the present invention is to provide a process for removing contaminants from a sulfolene-containing material with a solvent and recovering residual amounts of solvent from the purge gases utilized in the process.

Another object of the present invention is to provide an improved process for purifying sulfolene-containing materials in which a solvent is utilized to remove sulfur dioxide and the sulfur dioxide is removed from the solvent by an aqueous material with the residual water being removed from the solvent by azeotropic distillation.

A further object of the present invention is to provide an improved process for the purification of a sulfolane-containing material in accordance with previous object in which the residual water is removed as an azeotropic distillate.

Still another object of the present invention is to provide a process for the hydrogenation of sulfolene to sulfolane which results in more complete conversion.

A further object of the present invention is to provide an improved process for the hydrogenation of sulfolene to sulfolane in which the conversion time is significantly shortened.

Another and further object of the present invention is to provide an improved process for the hydrogenation of sulfolene to sulfolane which essentially eliminates the formation of nickel sulfate when Raney nickel is used as a catalyst.

A further object of the present invention is to provide an improved process for the hydrogenation of sulfolene to sulfolane and the recovery of sulfolane therefrom which reduces energy consumption.

Yet another object of the present invention is to provide an improved process for the hydrogenation of sulfolene to sulfolane which utilizes lower volumes of solvent.

Yet another object of the present invention is to provide an improved process for the hydrogenation of sulfolene to sulfolane which provides for faster and more complete separation of catalyst.

Another object of the present invention is to provide an improved process for the hydrogenation of sulfolene to sulfolane in which the $SO_2$ stability of the sulfolane product is improved.

In accordance with the present invention, a solfolene, containing contaminating sulfur dioxide, is dissolved in a solvent selected from a group consisting of alcohols and ketones having at least 6 carbon atoms per molecule and the sulfolene solution is stripped under conditions and for a time sufficient to reduce the sulfur dioxide content of the sulfolene solution. In addition to this treatment or in combination with such a treatment, a material containing sulfolene is converted to a sulfolane product be contacting the sulfolene with a solvent selected from the group consisting of alcohols and ketones having at least 6 carbon atoms per molecule, hydrogen, and a hydrogenation catalyst under conditions sufficient to convert the sulfolene to sulfolane.

BRIEF DESCRIPTION OF THE DRAWING

Other objects, aspects, and features of the present invention will be evident from the following detailed description of the invention, the claims and the drawing in which:

DESCRIPTION OF THE PREFERRED EMBODIMENTS

Figure 1:
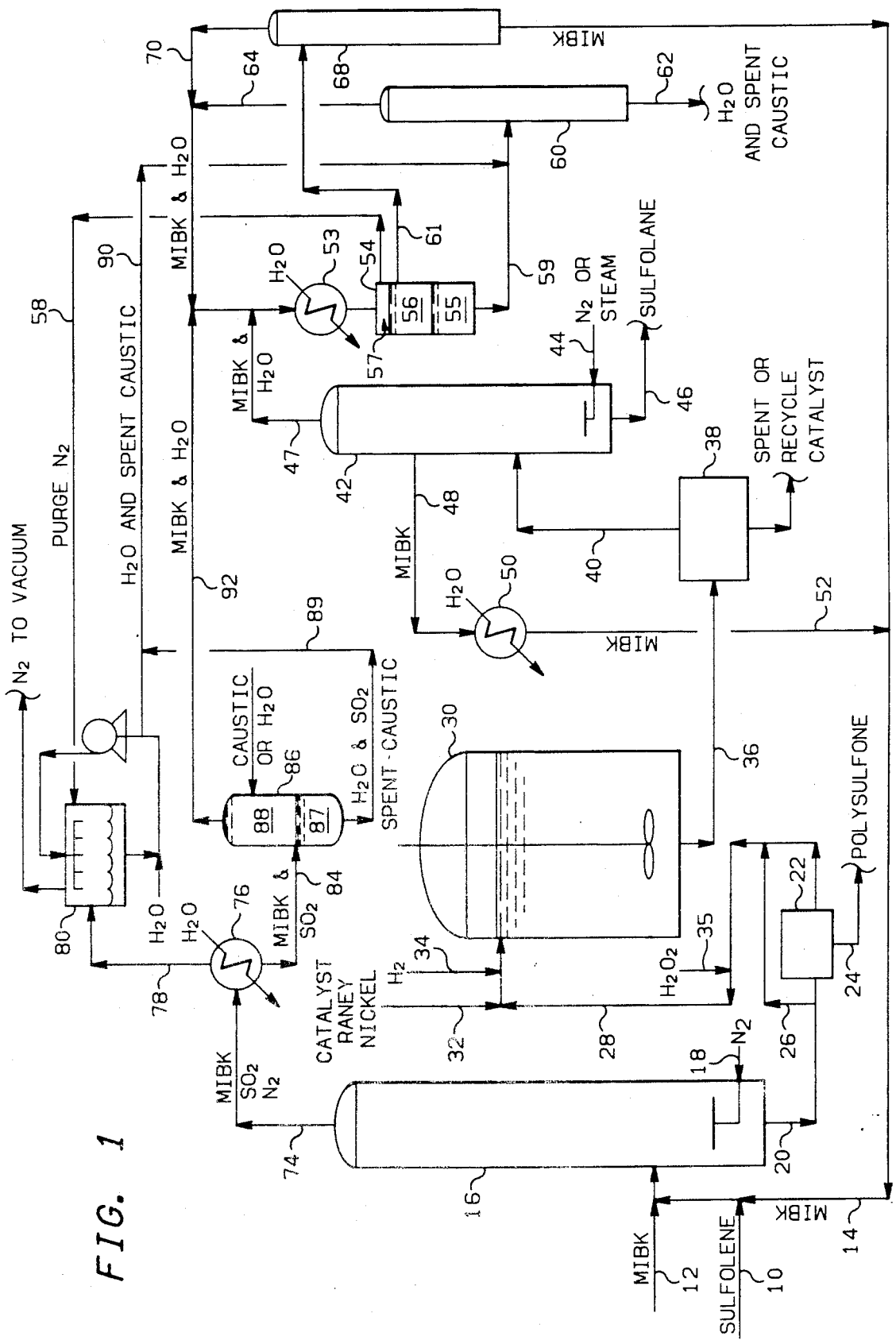
FIG. 1 is a schematic diagram illustrating a preferred embodiment of the present invention.

The terms "sulfolene-containing material" and "sulfolene feed" employed herein and in the appended claims generically defines the unsubstituted and substituted unsaturated compounds comprising or containing a sulfolene nucleus, i.e. a five-membered ring of four carbons atoms and a sulfur atom, a single olefinic linkage between any two adjacent carbon atoms of said ring and two oxygen atoms each of which is directly attached to the sulfur atom thereof. The most common sulfolene compounds are 3-sulfolene and 2-sulfolene.

Similarly, the terms "sulfolane", "sulfolane compound", "sulfolane-containing materials" and "sulfolane product" as utilized herein refer to saturated sulfolene compounds corresponding to the precursor sulfolene compound utilized as a feed material in the production of a sulfolane. Specifically, the sulfolane compound consists of a saturated five-membered ring of four carbon atoms and a sulfur atom, the latter having tow oxygen atoms directly attached thereto. The sulfolane compound will, of course, also include the substituted derivatives of the substituted sulfolenes. A complete description of sulfolenes and sulfolanes is included in U.S. Pat. No. 2,578,565 which is incorporated herein by reference.

As previously indicated, sulfolene compounds are generally prepared by the reaction of sulfur dioxide with a sulfolene precursor such as a conjugated diene, for example, butadiene, which results in production of a sulfolene compound generally containing minor amounts of sulfur dioxide and polysulfones. The amount of sulfur dioxide impurity present in a sulfolene feed and that which is formed during the hydrogenation of sulfolene will vary depending upon such factors as the efficiency of the recovery, purification of the sulfolene feedstock, the age of the sulfolene feedstock, temperatures during its storage and handling, hydrogenation reaction temperatures, and many other factors. Generally, the amount of contaminating sulfur dioxide will vary from about 0.005 to about 0.5 weight percent of the sulfolene feedstock or higher.

In accordance with one aspect of the present invention, a sulfur dioxide contaminant is removed from the sulfolene feedstock by pretreatment with a solvent selected from the group consisting of alcohols and ketones having at least six carbon atoms per molecule, slight solubility in water and boiling points above about 100° C. Suitable solvents of this character are methyl isobutyl ketone, methyl isobutyl carbinol, methy n-butyl carbinol, and others. The preferred solvent is methyl isobutyl ketone and will be referred to hereinafter in the description and examples. The solvent is preferably essentially anhydrous and, by its nature, can be readily separated for recycle in an anhydrous form in spite of the fact that small amounts of water are added during subsequent processing. Generally, the solvent is added to the sulfolene feed in amounts ranging from about 25 to about 100 percent by volume. The amount depends upon the balancing of energy requirements, and other factors, at later stages in the system. For example, using more solvent than is necessary increases the time and energy required to recover the excess solvent after hydrogenation of the sulfolene. On the other hand, using more solvent results in more efficient contact with the hydrogenation catalyst and somewhat faster catalyst settling and separation after hydrogenation. However, on balance, it is preferred that the lower concentrations of solvent be utilized. The solvent and sulfolene feed are fed to a sulfur dioxide purge column where a certain amount of the solvent and sulfur dioxide are stripped by passing an inert purging gas, such as nitrogen, through the column. As will be pointed out hereinafter with reference to the drawing, sulfur dioxide may be essentially purged in preparing sulfolene feed and the solvent recovered for reuse or recycle.

To the extent that the stripping and purging with solvent as previously described fails to remove sufficient sulfur dioxide, the sulfolene feed may be further treated with hydrogen peroxide. This treatment may be carried out either after the stripping and purging step previously described or before the hydrogenation reactor. In either event, the amount of hydrogen peroxide used will be sufficient to oxidize the sulfur dioxide to sulfur trioxide, a slight excess of hydrogen peroxide being preferred. The hydrogen peroxide may be added to the feed of the hydrogenation reactor, preferably, as aqueous hydrogen peroxide having a hydrogen peroxide concentration ranging from about 1 to about 50 weight percent. As will be hereinafter seen, small amounts of water are readily removed from the solvents of the present invention at the later stages of the system. To the extent that it is desired to remove polysulfones from sulfolene feed, the feed from the stripping and purging step is passed through a suitable filter which will remove essentially all of the polysulfones. The solvents of the present invention appear to have a very small affinity for polysulfones and, therefore, the polysulfones are readily separated by filtering.

The pretreated and optionally filtered sulfolene feed is fed to a hydrogenation reactor wherein it is contacted with hydrogen and a suitable hydrogenation catalyst to convert the sulfolenes to sulfolanes. Suitable hydrogenation catalysts include any of those known in the art for the catalytic hydrogenation of sulfolenes to sulfolanes. The preferred class of hydrogenation catalysts are those which comprise a metal hydrogenation catalyst such as those containing nickel, cobalt, copper, platinum, palladium or mixtures of these metals as well as mixtures of these metals with other metals such as iron, zinc, chromium, cadmium, and the like. These materials can be used in finely divided form, such as Raney nickel powder, or they can be suitably supported on a support, such as kieselguhr, aluminum oxide, diatomaceous earth and the like. Raney nickel catalysts, however, are preferred.

The reaction temperatures and pressures can vary over a wide range. In fact, any temperature is operable as long as it is a temperature whereby the reaction mixture is liquid and where it is below a temperature at which the material decomposes. The hydrogenation can generally be carried out at temperatures in the range of about 40 to about 80° C. and, preferably, in the range of about 55 to about 60° C. Pressure is generally in the range of about 100 to about 1000 psig, preferably between the 300 and about 600 psig. The time of treatment will depend upon the temperature and pressure employed and the effectiveness of catalyst poison removal, but it will generally be in the range of about 30 minutes to about 6 hours and, preferably, in the range of about 1 to about 2 hours.

The amount of catalyst can vary over wide ranges. Generally, however, the amount of Raney nickel catalyst would be about 0.01 to 0.1 weight percent of the sulfolene feed. As previously indicated, the sulfolene feed is normally solid material and, accordingly, it is preferred that the hydrogenation be carried out with the feed in a liquid state by maintaining it above its melting point and below the thermal decomposition temperature thereof, or in a solution of a suitable diluent such as water, benzene, or dioxane. The usual diluent is water. However, in accordance with the second aspect of the present invention, the solvent utilized in the stripping and purging of $SO_2$ from sulfolene feed is also utilized and is highly effective as a solvent for the hydrogenation of the sulfolene feed. Accordingly, as previously indicated, the amount of solvent in the sulfolene feed passed to the hydrogenation reactor is important and, therefore, stripping and purging should be carried out so that the effluent from the stripping and purging column of the sulfolene feed to the hydrogenation reactor should contain between about 25 volume percent to about 100 volume percent of solvent based on the volume of sulfolene feed.

As previously indicated, the solvent employed is essentially anhydrous and the only water present during the hydrogenation reaction are the small amounts of water necessary to form a slurry of the Raney nickel catalyst (for safety reasons) and the small amounts of water utilized in the hydrogen peroxide treatment, if such treatment is necessary or desirable.

Following hydrogenation, the catalyst is removed from the sulfolane product by filtering. This separation is also aided by the general characteristics of the solvent employed, particularly its specific gravity as compared with water. The catalyst thus removed may be disposed of, if spent, or recycled to the hydrogenation reaction, as appropriate.

Small amounts of water and the last traces of solvent can be recovered from the sulfolane product by azeotropic distillation in a solvent removal column. Preferably, the azeotropic distillation is carried out in the presence of an inert gas but, preferably, steam stripping and purging. The solvent forms a low boiling azeotrope with water, for example, Methyl Isobutyl Ketone (MIBK) forms an azeotrope which distills at 87.9° C. and contains 24.3 weight percent of water. Accordingly, in the course of the azeotropic distillation, this azeotrope is distilled overhead. Essentially anhydrous MIBK is withdrawn at essentially the boiling point of the MIBK (116.2° C.) and the purified sulfolane product is withdrawn as a bottoms product. A side stream of essentially anhydrous MIBK is returned to the initial stripping and purging column for reuse.

The azeotropic mixture of MIBK and water can be readily condensed by indirect heat exchange with water to form two separate, distinct liquid phases. The bottom aqueous phase is essentially saturated with MIBK solvent and the upper solvent phase contains similar quantities of water. Azeotropic distillation and the relatively low solubility of MIBK in water and water in MIBK allow for simple and easy recovery of MIBK from the aqueous phase and removal of water from the MIBK phase for recycle.

The overhead vapor from the initial stripping and purging step can be contacted by indirect heat exchange with water to form a liquid solvent containing some dissolved sulfur dioxide, which subsequently can be water washed or caustic washed to remove the dissolved sulfur dioxide. When the amount of solvent removed in the stripping and purging operation exceeds the solubility of the solvent in water or caustic, it will accumulate as an upper phase in the treater. This upper phase is accumulated and added to similar streams being returned to the separator of the solvent removal column.

After indirect heat exchange with water, the uncondensed gases comprising primarily nitrogen ($N_2$) and sulfur dioxide ($SO_2$) from the stripping and purging operation and any entrained solvent is further treated by passing the same through a water trap to remove entrained amounts of solvent therefrom. As needed, the water and dissolved solvent from this trap can be charged to the MIBK azeotropic distillation column where water or spent caustic containing sulfur dioxide is recovered as a liquid and where an azeotrop of MIBK and water is driven overhead. The overhead streams from the azeotropic distillation of MIBK, from the distillation of the removal of water from MIBK, and from the sulfolane azeotropic distillation can be combined with any solvent recovered from the caustic or water washing step. These combined streams are then passed to a condenser where heat is indirectly exchanged with water, or any other suitable heat exchange medium, to form two separate, distinct liquid phases. As previously mentioned, these phases are composed of a bottom aqueous phase, which is essentially saturated with MIBK solvent, and an upper solvent phase saturated with a small quanitity of water. The bottom aqueous phase is charged to the MIBK azeotropic distillation column. The upper solvent phase is charged to the distillation column for the removal of water from MIBK where essentially anhydrous MIBK is removed as a bottom product and recycled back to be mixed with sulfolene feed to the initial stripping and purging step of the process. An azeotrope of MIBK and water is taken overhead.

The best mode of operating the present process is illustrated by the single FIG. 1 wherein Methyl Isobutyl Ketone (MIBK) is utilized as a stripping and purging solvent for the removal of sulfur dioxide from sulfolene feed and as a solvent in the hydrogenation of sulfolene feed to sulfolane product.

In accordance with FIG. 1, sulfolene feed containing contaminating amounts of sulfur dioxide is introduced to the system through line 10. Make-up MIBK and recycled MIBK are introduced through lines 12 and 14, respectively. The mixture of MIBK and sulfolene feed is introduced to sulfur dioxide stripping column 16 or, alternatively, purging column 16, for the purpose of pretreating the sulfolene feed. An inert stripping or purge gas, such as nitrogen, is introduced through line 18. Since substantially all of the MIBK can be recovered as essentially anhydrous MIBK, little or no makeup MIBK is necessary. However, as previously pointed out, the amount of MIBK mixed with the sulfolene feed and charged to stripping column 16 should range from about 25 volume percent to about 100 volume percent, based on the volume of sulfolene feed charged through line 10 to stripping column 16. Pretreated sulfolene feed is removed through line 20 as a bottoms product from stripping column 16. To the extent that the pretreated sulfolene feed contains contaminating amounts of polysulfones, the bottoms product in column 16 is passed through filter 22 and polysulfones removed through line 24. If insignificant amounts of polysulfones are present, filter 22 can be bypassed through line 26. The sulfolene feed, which has been thus pretreated and clarified, is introduced through line 28 to hydrogenation reactor 30. An aqueous slurry of Raney nickel catalyst is added to the sulfolene feed through line 32 and hydrogen is added through line 34.

As previously indicated, if sulfur dioxide removal in column 16 is insufficient, further treatment with aqueous hydrogen peroxide may be necessary or desirable. Aqueous hydrogen peroxide may be added through line 35 to the sulfolene feed after stripping column 16 and before hydrogenation reactor 30. The hydrogenation reactor 30 may be any suitable type of reactor, however, it is preferable to use a batch-type stirred reactor. The effluent from hydrogenation reactor 30 is passed through line 36 to filter 38 where catalyst is removed from the hydrogenation product. To the extent that catalyst is spent, it may be disposed of or, if still active, it may be recycled to the hydrogenation reactor 30.

Liquid hydrogenation product from filter 38 is passed through line 40 to solvent removal column 42. The liquid hydrogenation product is stripped or purged in solvent removal column 42 with an inert gas such as nitrogen but, preferably with steam, which is introduced through line 44. The sulfolane product is recovered as a liquid bottoms product through line 46. This is in contrast to prior art practice of removing the sulfolane product as an overhead or distillate. Any quantities of water introduced with the Raney nickel catalyst, and hydrogen peroxide when used, can be readily removed as an overhead product of the solvent removal column 42 as an azeotropic mixture through line 47. An essentially anhydrous MIBK solvent stream can be removed from a medial portion of solvent removal column 42 through line 48. The MIBK removed through line 48 can then be condensed in water cooled condenser 50 and returned for recycle through line 52. Steam stripping in column 42 is preferred to remove the last traces of MIBK solvent from the sulfolane product. The azeotrope of MIBK and water contained as an overhead vapor from solvent removal column 42 is condensed in water cooled condenser 53 and passes to phase separator 54 where an essentially water phase 55, solvent phase 56, and an essentially inert gas phase 57 are formed. Because of the density differential between the two liquid phases, water phase 55 settles to the lower portion of phase separator 54 and solvent phase 56 forms above water phase 55. Water phase 55 is essentially water saturated with MIBK solvent. Water phase 55 is charged to MIBK recovery column 60 through line 59 where an azeotropic distillation is performed. Prior to entering MIBK recovery column 60, the water phase which is drawn from phase separator 54, is mixed with the spent caustic or water taken from the stripping column 16 overhead treating system. An azeotropic vapor is driven overhead from MIBK recovery column 60 through line 64 to water cooled condenser 53 and water or spent caustic is removed through line 62 as a bottoms product.

The solvent phase 56 is taken from phase separator 56 and charged to water removal column 68 through line 61. In water removal column 68, water is removed by azeotropic distillation with the azeotrope of water and MIBK being driven overhead through line 70 to water cooled condenser 53. The bottoms product of water removal column 68 is essentially anhydrous MIBK which is discharged into line 14 where it is recycled to mix with incoming feed through line 10 or where it is removed to storage. The essentially inert gas phase 57, which can contain entrained MIBK solvent, passes from phase separator 54 by way of line 58 to stripping column 16 overhead treating system for trapping out the entrained solvent.

Stripping column 16 is operated under reduced pressure and, preferably, under a vacuum where the conditions are such that contaminating sulfur dioxide contained within sulfolene feed 10 is swept overhead through line 74, along with purging gas and any MIBK solvent, to water cooled condenser 76. Noncondensible gases may further be passed through line 78 and dispersed through water trap 80 to collect entrained MIBK solvent, which is discharged into line 90. The high boiling point (115.8° C.) of MIBK allows for the vacuum purging of contaminating sulfur dioxide from sulfolene feed using an inert gas sweep while still allowing for the condensation of overhead vapors with cooling water condensers.

Because of the low solubility of MIBK in water, any dissolved sulfur dioxide in the MIBK solvent may easily be removed by water or caustic washing in scrubbing vessel 86. This is accomplished by passing the solvent containing sulfur dioxide through line 84 to water or caustic washing unit 86 where it is contacted with caustic or water and two phases are formed. Lower liquid phase 87 containing either caustic, or water, or both, having sulfur dioxide which is scrubbed from the MIBK solvent that is driven overhead from stripping column 16 is further passed through line 89 to combine with water from water trap 80 and sent to MIBK recovery column 60 through line 90. The upper liquid phase 88 of caustic washing unit 86, which comprises essentially the solvent MIBK, is passed through line 92 to water cooled condenser 53.

EXAMPLE I

To show the advantages from using higher molecular weight alcohols and ketones as solvents for the economical hydrogenation of sulfolene in the presence of a hydrogenation catalyst such as Raney nickel, a series of tests were performed using MIBK and other compounds as a hydrogenation solvent. These tests unexpectedly show that the hydrogenation of sulfolene can be suitably carried out using a high molecular weight ketone such as MIBK in place of other lower molecular weight solvents. The advantage from being able to use MIBK, as opposed to using the lower molecular weight solvents, is that it has a higher boiling temperature which allows the vacuum purging of sulfolene using an inert gas sweep such as nitrogen to remove contaminating sulfur dioxide ($SO_2$) from sulfolene feed. Another advantage of using MIBK as a solvent is the low solubility of the solvent MIBK in water and of water in the solvent MIBK. With a low MIBK solubility in water, any SO₂ dissolved in the MIBK solvent can easily be removed by a water or caustic washing. Furthermore, because of the low solubility of water in MIBK, the MIBK can more easily be dried by azeotropic distillation. The water-MIBK azeotrope is formed in the vapor overhead of an azeotropic distillation vessel and, when it is condensed, two phases comprising a water phase and an MIBK solvent phase are formed which allow for easy separation. Because of the above indicated advantages, if MIBK can be suitably used as a hydrogenation solvent which gives a high sulfolene conversion to sulfolane at reasonable reaction rates and catalyst consumption, then the use of MIBK as a solvent can provide certain process advantages in the removal of SO₂ from sulfolane feed and in the separation of end products and solvent. The following tests were performed to determine the suitability of MIBK as a hydrogenation solvent.

Six hundred (600) grams of flaked sulfolene was dissolved in 500 milliliters of solvent in a two (2) liter round bottom flask equipped with a thermowell and a nitrogen purge line. Solvent was distilled overhead while simultaneously purging the flask with inert nitrogen (N₂) gas until essentially no sulfur dioxide remained in the sulfolene solution. Make-up solvent was added to the kettle to replace the solvent which was distilled during the purging operation. During the purging operation, a vacuum was maintained in the flask by a water aspiration to allow a low temperature distillation for minimizing sulfolene decomposition. After the purging step, the solution of sulfolene and solvent was transferred to a two (2) liter Parr reactor. Added to the solution was one (1) gram of hexamethylenetetramine (HMTA) and forty (40) grams of Raney nickel catalyst. The reactor was flushed with hydrogen gas and then pressured to 300 psig. The hydrogenation reaction was controlled at 140° F. and 300 psig for a period of one and one-half (1.5) hours. The following Table I gives the results of this test in terms of percent conversion of sulfolene to sulfolane for each of the hydrogenation solvents tested. As can be seen from Table I, MIBK provides a percent conversion which is comparable to that of other hydrogenation solvents.

TABLE I

| Solvent | Run No. | Percent Conversion |
| --- | --- | --- |
| Acetone | Run 1 | 99.9 |
|  | Run 2 | 99.7 |
|  | Run 3 | 98.2 |
|  | Run 4 | 99.9 |
|  | Average | 99.4 |
| Tetrahydrofuran (THF) | Run 1 | 100 |
|  | Run 2 | 97.8 |
|  | Average | 98.9 |
| Methyl Ethyl Ketone (MEK) | Run 1 | 99.7 |
|  | Run 2 | 99.9 |
|  | Average | 99.8 |
| Methyl Isobutyl Ketone (MIBK) | Run 1 | 95.8 |
|  | Run 2 | 99.5 |
|  | Average | 97.7 |

While specific materials, conditions of operation, modes of operation and equipment have been referred herein, it is to be recognized that these and other specific recitals are for illustrative purposes and to set forth the best mode only and are not to be considered limiting.

That which is claimed is:

1. A process for the purification of a sulfolene feed containing contaminating amounts of sulfur dioxide, comprising:
   (a) dissolving said sulfolene feed in a solvent selected from the group consisting of alcohols and ketones having at least six carbon atoms per molecule, a slight solubility in water and a boiling point significantly above 100° C.; and
   (b) distilling the thus produced sulfolene solution under conditions and for a time sufficient to reduce the amount of sulfur dioxide in said sulfolene feed.

2. A process in accordance with claim 1 wherein the solvent is methyl isobutyl ketone.

3. A process in accordance with claim 1 wherein the distillation is carried out with an inert gas purge.

4. A process in accordance with claim 3 wherein the purged overhead from step (b) is cooled by indirect heat exchange with water to form a solvent phase containing dissolved sulfur dioxide, said solvent phase is washed with an aqueous liquid to remove said sulfur dioxide and a solvent phase, said solvent phase is separated to recover an essentially anhydrous solvent therefrom and said essentially anhydrous solvent is recycled to step (a).

5. A process in accordance with claim 4 wherein the cooling step of claim 4 produces a vapor phase containing residual solvent, said vapor phase is passed through a water trap to form an aqueous phase containing said residual solvent and said residual solvent is recovered in an essentially anhydrous form and recycled to step (a).

6. A process for converting a sulfolene feed, containing contaminating amounts of sulfur dioxide, to a sulfolane product, comprising:
   (a) dissolving said sulfolene feed in a solvent selected from the group consisting of alcohols and ketones, having at least six carbon atoms per molecule, slight solubility in water and a boiling point significantly above 100° C.;
   (b) stripping the thus produced sulfolene solution under conditions and for a time sufficient to reduce the amount of sulfur dioxide in said sulfolene solution;
   (c) contacting said sulfolene solution and hydrogen with a hydrogenation catalyst, under conditions and for a time sufficient to convert said sulfolene feed to said sulfolane product; and
   (d) recovering said sulfolane product from the effluent of step (c).

7. A process in accordance with claim 6 wherein the solvent is methyl isobutyl ketone.

8. A process in accordance with claim 6 wherein the catalyst is a Raney nickel catalyst.

9. A process in accordance with claim 6 wherein stripping step (b) utilizes an inert gas purge.

10. A process in accordance with claim 6 wherein a small amount of water is present during contacting step (c) and the sulfolane product is recovered from the effluent of step (c) by steam stripping to recover an azeotrope of the solvent and the water as an overhead, essentially anhydrous solvent as a side stream and said sulfolane product as a bottoms product, and said essentially anhydrous solvent is recycled to step (a).

11. A process in accordance with claim 6 wherein a small amount of water is present during contacting step (c) and the sulfolane product is recovered from the effluent of step (c) by azeotropic distillation to recover an azeotrope of the solvent and the water as an overhead, essentially anhydrous solvent as a side stream and said sulfolane product as a bottoms product, and said essentially anhydrous solvent is recycled to step (a).

12. A process in accordance with claim 11 wherein the azeotrope of solvent and water is separated by cooling said azeotrope by indirect heat exchange with water to form a solvent phase and an aqueous phase, and said solvent phase is distilled to form a bottoms product comprising essentially anhydrous solvent, an overhead phase comprising an azeotrope of said solvent and water and said essentially anhydrous solvent phase is recycled to step (a).

13. A process in accordance with claim 12 wherein the aqueous phase separated in claim 12 is distilled to produce an aqueous bottoms phase and an azeotrope of solvent and water as an overhead and the azeotrope produced by claim 12 and the azeotrope produced in claim 8 are combined with the azeotrope produced by the azeotropic distillation of claim 6.

14. A process in accordance with claim 13 wherein the purged overhead of step (a) is cooled by indirect heat exchange with water to form a mixture of solvent and dissolved sulfur dioxide, the sulfur dioxide is removed from the mixture by washing with an aqueous liquid to form an aqueous phase containing said sulfur dioxide and a solvent phase, said solvent phase is combined with the azeotrope formed in claim 13 and the aqueous phase is combined with the aqueous phase formed in claim 12.

15. A process in accordance with claim 12 wherein the purged overhead from step (a) is cooled by indirect heat exchange with water to form a liquid phase comprising solvent and dissolved sulfur dioxide, the sulfur dioxide is removed from the mixture by washing with an aqueous liquid to form an aqueous phase containing the sulfur dioxide and a water saturated solvent phase, the solvent phase is combined with the azeotrope formed in claim 12 and the aqueous phase is combined with the separated aqueous phase of claim 12.

16. A process in accordance with claim 15 wherein the aqueous liquid is a caustic solution.

17. A process in accordance with claim 15 wherein a vapor phase formed by the cooling in claim 12 is passed through a water trap to remove residual solvent therefrom and the water containing the thus removed solvent is combined with the aqueous phase produced by the cooling step in claim 12.

* * * * *